(12) United States Patent
Walsh et al.

(10) Patent No.: US 8,079,980 B2
(45) Date of Patent: Dec. 20, 2011

(54) SINGLE USE SYRINGE

(75) Inventors: Allan Walsh, Medowie (AU); Feiyan Tan, Foshan (CN)

(73) Assignee: Morgan Meditech Inc., Kowloon (HK)

( * ) Notice: Subject to any disclaimer, the term of this patent is extended or adjusted under 35 U.S.C. 154(b) by 0 days.

(21) Appl. No.: 12/304,899

(22) PCT Filed: May 25, 2007

(86) PCT No.: PCT/AU2007/000725
§ 371 (c)(1),
(2), (4) Date: Dec. 15, 2008

(87) PCT Pub. No.: WO2008/128273
PCT Pub. Date: Oct. 30, 2008

(65) Prior Publication Data
US 2010/0036315 A1 Feb. 11, 2010

(30) Foreign Application Priority Data
Apr. 24, 2007 (AU) .............................. 2007902162

(51) Int. Cl.
*A61M 5/00* (2006.01)
(52) U.S. Cl. ....................................................... 604/110
(58) Field of Classification Search ............... 604/93.01, 604/110, 181, 187, 192, 218
See application file for complete search history.

(56) References Cited

U.S. PATENT DOCUMENTS

| | | |
|---|---|---|
| 4,775,364 A | 10/1988 | Alles |
| 4,932,941 A | 6/1990 | Min et al. |
| 5,059,181 A | 10/1991 | Agran ............................ 604/110 |
| 5,415,638 A | 5/1995 | Novacek et al. |
| 5,578,015 A | 11/1996 | Robb |
| 5,980,487 A * | 11/1999 | Jones et al. .................... 604/110 |
| 5,997,511 A | 12/1999 | Curie et al. .................... 604/195 |

(Continued)

FOREIGN PATENT DOCUMENTS

CN 2488527 Y 5/2002

(Continued)

OTHER PUBLICATIONS

PCT International Search Report based on PCT/AU2006/001228 dated Nov. 10, 2006.

(Continued)

*Primary Examiner* — Jackie Ho
*Assistant Examiner* — Victoria P Campbell
(74) *Attorney, Agent, or Firm* — Greenberg Traurig, LLP; David J. Dykeman; Roman Fayerberg (57) ABSTRACT

A single use syringe is disclosed having a leading end, a trailing end and a longitudinal axis. The syringe comprises a longitudinally extending hollow barrel, a plunger having a stem, a head and a needle tip. The head being longitudinally displaceable within the barrel. The stem having a first engagement formation and the head having a shoulder defining a second engagement formation. A locking bush is longitudinally fixed within the barrel, the bush having an aperture adapted to receive the stem, permitting the stem to slide longitudinally relative to the bush. The bush has a third engagement formation, and the bush also has an abutment surface defining a fourth engagement formation. The plunger is longitudinally displaceable in a retraction direction away from the leading end to a captive position in which the first engagement formation captively engages the third engagement formation thereby preventing the stem from being longitudinally displaced in an insertion direction toward the leading end from the captive position. The fourth engagement formation is engageable with the second engagement formation if an attempt is made to longitudinally displace the stem in the retraction direction from the captive position.

12 Claims, 8 Drawing Sheets

U.S. PATENT DOCUMENTS

| | | | | |
|---|---|---|---|---|
| 6,033,385 | A * | 3/2000 | Liu | 604/195 |
| 6,482,174 | B2 | 11/2002 | Tiu | |
| 6,669,666 | B2 | 12/2003 | Lu | 604/110 |
| 6,911,018 | B2 * | 6/2005 | Gordon | 604/110 |
| 6,929,622 | B2 * | 8/2005 | Chian | 604/110 |
| 6,989,001 | B2 * | 1/2006 | Chen | 604/110 |
| 2001/0021821 | A1 * | 9/2001 | Wang et al. | 604/110 |
| 2002/0156396 | A1 | 10/2002 | Tiu | |
| 2003/0060778 | A1 | 3/2003 | Lu | 604/240 |
| 2003/0158525 | A1 | 8/2003 | Thorley et al. | 604/240 |
| 2004/0082911 | A1 | 4/2004 | Tiu et al. | |
| 2004/0176722 | A1 | 9/2004 | Capes et al. | |
| 2005/0033228 | A1 * | 2/2005 | Wang | 604/110 |
| 2005/0113751 | A1 | 5/2005 | Chen | |
| 2005/0240149 | A1 | 10/2005 | Lu | |
| 2005/0267411 | A1 * | 12/2005 | Chen | 604/110 |
| 2006/0052748 | A1 * | 3/2006 | Coelho et al. | 604/110 |
| 2006/0111668 | A1 * | 5/2006 | Baik | 604/110 |
| 2007/0073245 | A1 * | 3/2007 | Shih | 604/198 |
| 2007/0149923 | A1 * | 6/2007 | Chen | 604/110 |
| 2007/0173758 | A1 * | 7/2007 | Chen | 604/110 |
| 2008/0262423 | A1 * | 10/2008 | Ingram et al. | 604/110 |
| 2009/0171287 | A1 * | 7/2009 | Walton et al. | 604/110 |
| 2009/0192457 | A1 | 7/2009 | Walsh et al. | |

FOREIGN PATENT DOCUMENTS

| | | |
|---|---|---|
| CN | 2595384 Y | 12/2003 |
| DE | 3833138 | 4/1990 |
| EP | 0409134 | 1/1991 |
| FR | 2787719 | 6/2000 |
| FR | 2821563 | 9/2002 |
| WO | WO 88/10127 | 12/1988 |
| WO | WO 93/05833 | 4/1993 |
| WO | WO 95/23004 | 8/1995 |
| WO | WO 01/80930 | 11/2001 |
| WO | WO 2005/072797 | 8/2005 |
| WO | WO 2006/047810 | 5/2006 |
| WO | WO 2006/119667 | 11/2006 |
| WO | WO 2007/131259 | 11/2007 |
| WO | WO 2008/128273 | 10/2008 |

OTHER PUBLICATIONS

Office Action in U.S. Appl. No. 12/300,742 mailed Jul. 20, 2010.
PCT International Search Report based on PCT/AU2007/000725 dated Jul. 13, 2007.

* cited by examiner

SINGLE USE SYRINGE

RELATED APPLICATIONS

This application is a national phase filing under 35 U.S.C. 371 of International Application No. PCT/AU2007/000725, filed on May 25, 2007, and claims the benefit of Australia Application Number 2007902162, filed Apr. 24, 2007, the entirety of these applications are hereby incorporated herein by reference for the teachings therein.

FIELD OF THE INVENTION

The present invention relates to a single use syringe. In particular, the present invention relates to a single use syringe having a lock assembly for isolating the plunger relative to the syringe barrel.

BACKGROUND OF THE INVENTION

Retractable syringes attempt to reduce the risk of needle stick injuries which can result in the transmission of blood born diseases, such as Hepatitis and Human Immuno-deficiency Virus (HIV).

Retractable syringes may be either manually retractable syringes, or auto-retractable syringes. With manually retracting syringes, after an injection has been administered, the user pulls the plunger away from the leading end of the syringe resulting in the plunger and needle tip being pulled inside the barrel. This significantly reduces the risk of needle stick injuries. Similarly, with auto retractable syringes, when the injection has been administered the piston is pushed away from the leading end of the barrel by a spring or other such biasing means and the needle tip is accordingly retracted into the barrel.

In some instances, when the needle tip has been retracted, the trailing end of the plunger is manually snapped off by the medical practitioner at a designated shear point to reduce the likelihood of the syringe subsequently being reused.

With retractable syringes, a problem exists when the plunger is inadvertently completely withdrawn from the trailing end of the barrel again, exposing the needle tip. This exposes the medical practitioner and other persons to the needle tip, and accordingly increases the risk of needle stick injuries.

In addition, in many instances the plunger may subsequently be reloaded into the syringe barrel, enabling the reuse of the syringe. This is most undesirable on account of the inherent risk of blood borne disease transmission when syringes are not adequately sterilised and then reused. Disease transmission resulting from syringe reuse among intravenous drug users is well known. In addition, in developing nations, syringes are often reused for immunisations or other treatments without adequate sterilisation between patients.

In some types of retractable syringes where the plunger can be withdrawn after the plunger has reached the bottom of the stroke. The plunger is intended to stay in a closed position but may undesirably be tampered with by pulling the plunger back and subsequently reassembling the syringe for further use.

OBJECT OF THE INVENTION

It is an object of the invention to substantially overcome or at least ameliorate one or more of the above disadvantages, or at least to provide a useful alternative to existing syringes.

SUMMARY OF THE INVENTION

In a first aspect, the present invention provides a single use syringe having a leading end, a trailing end and a longitudinal axis, said syringe comprising:
a longitudinally extending hollow barrel,
a plunger having a stem, a head and a needle tip, said head being longitudinally displaceable within said barrel, said stem having a first engagement formation and said head having a shoulder defining a second engagement formation;
a locking bush longitudinally fixed within said barrel, said bush having an aperture adapted to receive said stem, permitting the stem to slide longitudinally relative to said bush, said bush having a third engagement formation, said bush also having an abutment surface defining a fourth engagement formation;
wherein said plunger is longitudinally displaceable in a retraction direction away from the leading end to a captive position in which said first engagement formation captively engages said third engagement formation thereby preventing the stem from being longitudinally displaced in an insertion direction toward the leading end from said captive position,
further wherein said fourth engagement formation is engageable with said second engagement formation if an attempt is made to longitudinally displace said stem in the retraction direction from said captive position.

The first engagement formation preferably includes a resilient finger, the finger being angularly offset relative to the longitudinal axis and directed generally towards the leading end of the syringe.

In a second aspect, the present invention provides a single use syringe having a leading end, a trailing end and a longitudinal axis, said syringe comprising:
a longitudinally extending hollow barrel,
a plunger having a stem, a head and a needle tip, said head being longitudinally displaceable within said barrel, said stem having a first engagement formation and said head having a shoulder defining a second engagement formation;
a locking bush longitudinally fixed within said barrel, said bush having an aperture adapted to receive said stem, permitting the stem to slide longitudinally relative to said bush, said bush having a third engagement formation,
a restriction within said barrel defining a fourth engagement formation,
wherein said plunger is longitudinally displaceable in an insertion direction toward the leading end to a captive position in which said first engagement formation captively engages said third engagement formation thereby preventing the stem from being longitudinally displaced in a retraction direction away from the leading end from said captive position,
further wherein said fourth engagement formation is engageable with said second engagement formation if an attempt is made to longitudinally displace said stem in the insertion direction from said captive position.

The first engagement formation preferably includes a resilient finger, the finger being angularly offset relative to the longitudinal axis and directed generally towards the trailing end of the syringe.

The third engagement formation preferably includes a shoulder formed within the aperture of the locking bush.

The stem preferably includes a web extending parallel to the longitudinal axis, a base portion of the finger being integrally formed with the web, further wherein the aperture formed in the locking bush includes a slot adapted to receive the web.

The stem preferably includes a plurality of the webs radially equi-spaced about the longitudinal axis, further wherein the aperture of the locking bush includes a plurality of radially equi-spaced slots adapted to receive the webs.

A circumferential outer wall of the locking bush preferably includes a fifth engagement formation which is engaged with a sixth engagement formation defined by an inner wall of the barrel to longitudinally fix the locking bush.

The fifth engagement formation preferably includes one or more shoulders and the sixth engagement formation includes one or more grooves.

The locking bush is preferably formed from two generally semi-circular segments.

The segments are preferably integrally formed and connected to each other with a flexible web.

In a third aspect, the present invention provides a method of assembling the syringe described above, said method including the steps of:

placing said generally semi-circular segments of said locking bush around the stem and closing the locking bush to substantially enclose a portion of said stem within the aperture of said locking bush;

inserting the stem into the barrel; and snapping the locking bush into a longitudinally fixed location within the barrel.

The step of snapping the locking bush into a longitudinally fixed location within the barrel preferably includes engaging a fifth engagement formation formed on a circumferential outer wall of the locking bush with a sixth engagement formation formed on an inner wall of the barrel.

BRIEF DESCRIPTION OF THE DRAWINGS

Preferred embodiments of the present invention will be described by way of example only, with reference to the accompanying drawings, in which.

DETAILED DESCRIPTION OF THE PREFERRED EMBODIMENTS

Figure 1:
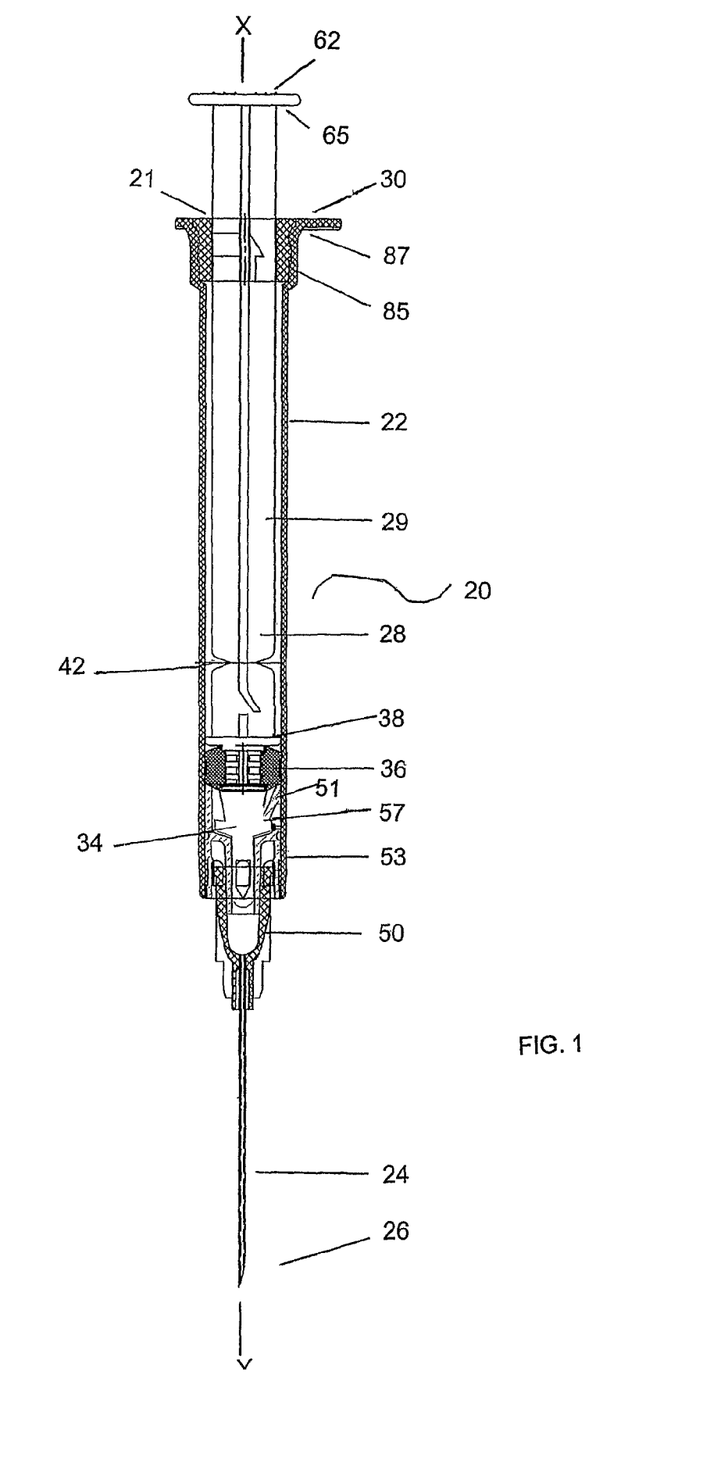
FIG. 1 is a partial sectional view of a syringe according to a first embodiment with the plunger head being located towards the leading end of the syringe.

A first embodiment of a single use retractable syringe is depicted in FIGS. 1 to 9 and indicated by the reference numeral 20. As seen in FIG. 1, the syringe 20 includes a hollow barrel 22 having a longitudinal axis X, a leading end 26 and a trailing end 30. The barrel 22 is in fluid communication with a stainless steel needle tip 24.

The barrel 22 is made from a clear plastic material enabling the volume of liquid contained therein to be externally seen.

Figure 3:
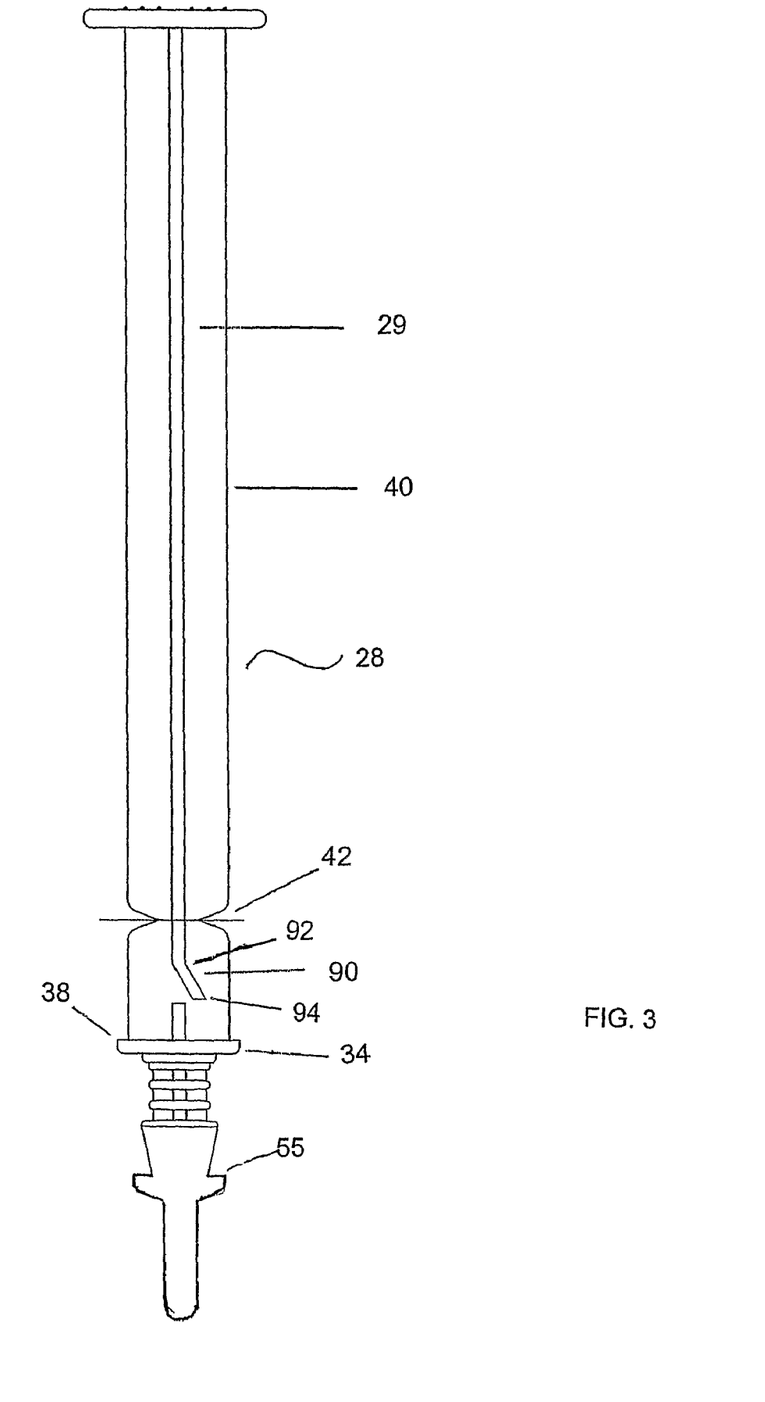
FIG. 3 shows the syringe plunger of FIG. 1.

The syringe 20 also includes a plunger 28 as shown in isolation in FIG. 3 which is insertable into an opening 21 formed in the end of the barrel 22 furthest from the leading end 26. The plunger 28 includes a head 34 and a stem 29 which is connected to the head 34. The plunger 28 also includes a finger pad 62, which is formed at an end of the plunger 28 furthest from the leading end 26. A rubber piston seal 36 is seated on the head, and provides a liquid tight seal against the internal wall of the barrel 22.

The stem 29 includes one or more webs 40 which extend in a direction parallel to the longitudinal axis X, and substantially the length of the stem 29. In the embodiment shown in the figures, there are four webs 40 which are radially equi-spaced about the longitudinal axis X, forming a cross-shape when viewed for example through a plane which extends perpendicular to the longitudinal axis X. In an alternative embodiment not shown in the drawings, there are three webs 40 generally forming a Y-shape when viewed for example through a plane which extends perpendicular to the longitudinal axis X. Alternatively, there may be only two webs.

As depicted in FIG. 1, the needle tip 24 is mounted on a needle hub 50 which is in turn mounted to a gland 53 that is slidable within the barrel 22 after an injection has been administered. The gland 53 has a locking formation 51 in the form of a flexible finger 51 which permits the gland 53 to engage with a corresponding locking formation 57 on the head 34 in the form of a shoulder 57, at the completion of an injection stroke.

In the first embodiment, the syringe 20 is manually retractable, such that the needle tip 24 is manually retracted into the barrel 22 by pulling the plunger 28 away from the barrel 22 toward the trailing end of the syringe 20. However, in another embodiment not shown in the drawings, the needle tip 24 is auto-retractable, such that after completion of an injection, a spring or other such biasing means (not shown in the drawings) urges the needle tip 24 to retract within the barrel 22.

As shown in FIG. 3, one or more of the webs 40 includes a first engagement formation in the form of a resilient finger 90 which has a fixed base portion 92 and a resilient tip 94. The finger 90 is angularly offset relative to the longitudinal axis X. The finger tip 94 is resiliently biased such that it is directed radially outwardly relative to the longitudinal axis when no force is applied to it. As seen in FIG. 3, the finger is also directed generally towards the leading end of the syringe 20. The finger 90 is integrally formed with the web 40 and as shown in FIG. 3, the finger 90 is defined by a break in the web 40.

A finger 90 may be arranged on each of the webs 40. Alternatively, the fingers 90 may be arranged on two opposing webs 40 as shown in FIG. 3, or alternatively, on one web 40 only.

The head has a second engagement formation defined by a rearwardly facing abutment shoulder 38. The shoulder 38 is located at the end of the head 34 furthest from the leading end 26, and the cross sectional area of the shoulder (in a plane extending perpendicular to the longitudinal axis X) is larger than the cross sectional area of the stem 29.

The stem 29 has a frangible region 42 located adjacent to the head 34. The frangible region 42 is formed by cut-outs formed in each of the webs 40, thereby reducing the cross-sectional area of the stem 29, and hence locally reducing the yield strength of the stem 29.

Figure 4:
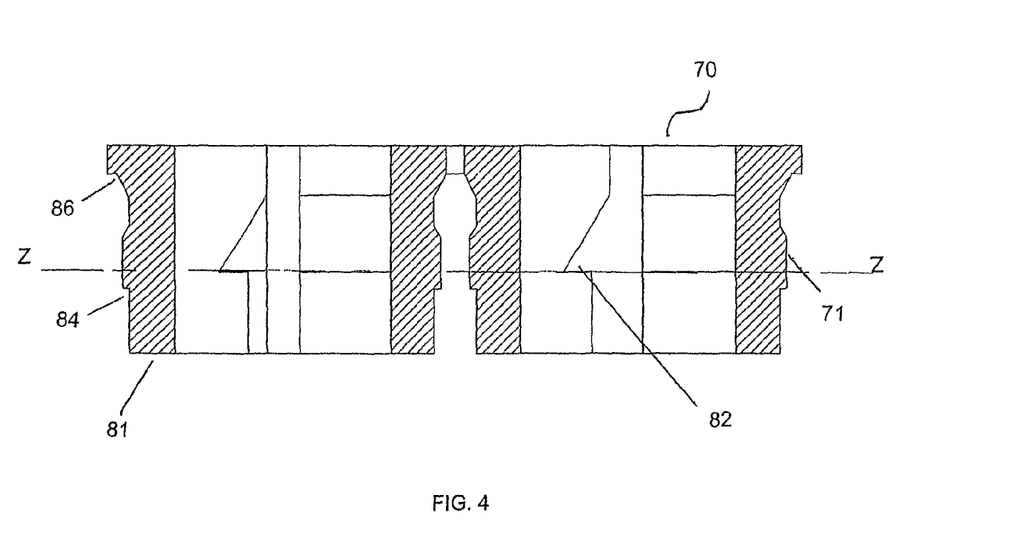
FIG. 4 is a side view depicting a locking bush in an open position.
Figure 5:
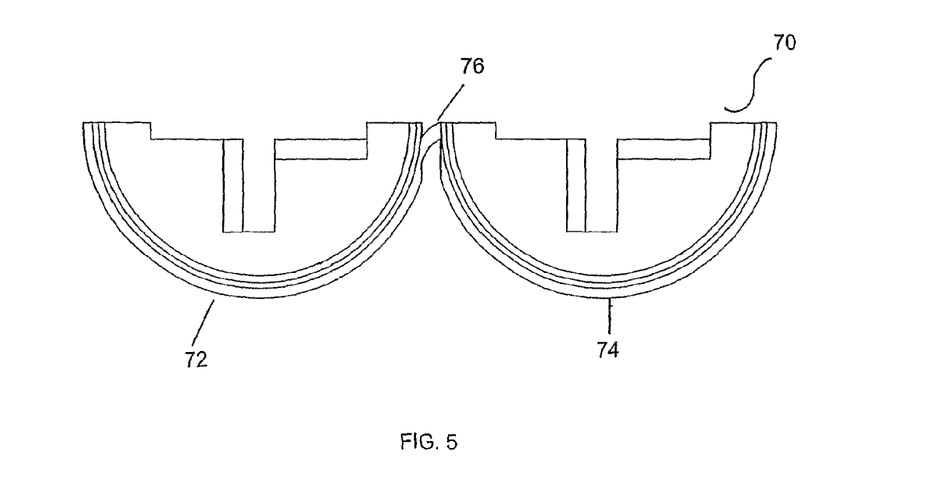
FIG. 5 is a bottom view of the locking bush of FIG. 4.
Figure 6:
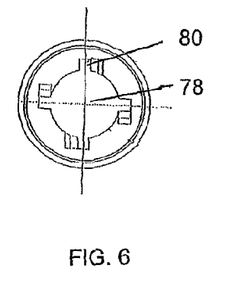
FIG. 6 is a bottom view of the locking bush in a closed position.

The syringe 20 includes a locking bush 70, shown in isolation in FIGS. 4 and 5. The locking bush 70 is formed from two generally semi-circular segments 72, 74. The segments 72, 74 may be integrally formed and connected to each other by an elastically deformable web 76. The web 76 is sufficiently flexible to permit the two segments 72, 74 to be closed into a complete circle. When arranged as a circle, the locking bush 70 has a central aperture 78 best seen in FIG. 6. The central aperture 78 includes a central circular opening and one or more radially extending slots 80. In the embodiment shown in the drawings, there are four slots 80 which are radially equi-spaced, defining a cross-shaped formation when viewed from either end of the locking bush 70, so as to match the configuration of four webs 40 of the stem 24.

As shown in FIG. 4, one or more of the slots 80 includes a third engagement formation in the form of a rearwardly facing shoulder 82. Each shoulder 82 locally defines an increase in the cross-sectional area of the slot 80, in a plane Z (see FIG. 4) which is perpendicular to the longitudinal axis X. The locking bush 70 includes a fourth engagement formation in the form of a forwardly facing abutment surface 81, formed by a generally annular end surface of the locking bush 70.

The outer circumferential wall 71 of the locking bush 70 includes a fifth engagement formation defined by one or more forwardly facing shoulders 84, 86 which are engageable with a corresponding sixth engagement formation defined by one or more grooves 85, 87 formed on the inner wall of the barrel 22.

During assembly of the syringe 20, the two segments 72, 74 of the locking bush 70, are placed around the stem 29 and the locking bush 70 is closed into a circle, such that the webs 40 are each positioned within one of the slots 80. The slots 80 in the locking bush 70 are slightly larger than the webs 40, such that the stem 29 is slidable through the locking bush 70.

The head 34 is inserted into the opening 21 of the barrel 22. When the plunger 28 is sufficiently loaded into the barrel 22, such that the stem 29 has started to enter the barrel 22, the locking bush 70 is pushed into the opening 21 of the barrel 22, such that the shoulders 84, 86 of the locking bush 70 engage with the corresponding grooves 85, 87 of the barrel 22. The locking bush 70 is then snapped into a longitudinally fixed position in the barrel 22, such that the fifth and sixth engagement formations captively engage each other.

The abutment surface 81 of the locking bush 70 radially projects into the barrel 22, thereby locally reducing the cross-sectional area of the cavity within the barrel 22.

The operation of the syringe 20 according to the first embodiment will now be described. When medication or an immunisation is to be administered, a medical practitioner removes the needle cap (not shown) which exposes the needle tip 24. The practitioner then applies a force with his/her thumb to the finger pad 62, to drive the stem 29 and accordingly the head 34 into the barrel 22, until the head 34 approaches the end of its stroke.

The user then inserts the needle tip 24 into a vial of liquid (not shown) and subsequently retracts the stem 29 away from the leading end 26 end of the syringe 20, to draw a desired quantity of the liquid into the barrel 22. Markings on the side of the barrel 22 indicate the volume of the liquid contained therein, such that a desired dosage of liquid can be measured.

The user then holds the syringe 20 with the needle tip 24 facing upwardly and applies a further force with his/her thumb to the finger pad 62, to again drive the head 34 in an insertion direction into the barrel 22 toward the leading end 26. Any air present in the barrel 22 is then expelled from the needle tip 24, leaving only liquid within the barrel 22.

The needle tip 24 is then inserted into a patient's tissue or a vein as required, and the contents of the barrel 22 are injected into the patient by applying further force to the finger pad 62 such that the head 34 moves in the barrel 22 in an insertion direction towards the leading end 26 of the syringe 20. When the head 34 approaches the end of its stroke, all of the liquid has been injected.

At the end of the insertion stroke, the locking formation defined by a shoulder 57 formed on the head 34 engages with the locking formation 51 in the form of a finger 51 formed on the gland 53. The head 34 accordingly locks together with the gland 53 which is secured to the needle hub 50. When the syringe 20 is of the manual retraction variety, the subsequent withdrawal of the stem 29 away from the leading end 26 causes the retraction of the needle hub 50 and hence the needle tip 24 into the barrel 22. Alternatively, when the syringe 20 is of the auto-retract variety, the spring or biasing means forces the needle hub 50 and the needle tip 24 to retract into the barrel 22.

Near the end of the retraction stroke, the needle tip 24 is completely sheathed within the barrel 22, and accordingly, the risk of needle stick injuries is reduced. By further retracting the stem 29, the fingers 90 enter into the slots 80 of the locking bush.

Whilst the syringe may be embodied with one or more fingers 90 on the stem 29, there are shoulders 82 in all of the slots 80 of the locking bush 70. That is, one shoulder 82 corresponds to each web formed on the stem 29. Accordingly, captive engagement between the locking bush 70 and the step 29 will always be achieved irrespective of the orientation of the stem. This means that there is no requirement to insert the stem 29 in a particular angular arrangement relative to the locking bush 70 during assembly of the syringe 20.

On account of the fingers 90 being biased radially outwardly away from the centre of the aperture 78, the fingers 90 resiliently contact the wall of the slots 80. The medical practitioner subsequently feels the contact between the fingers 90 and the slots 80, and is aware that the plunger 28 is nearing the end of the retraction stroke.

Figure 2:
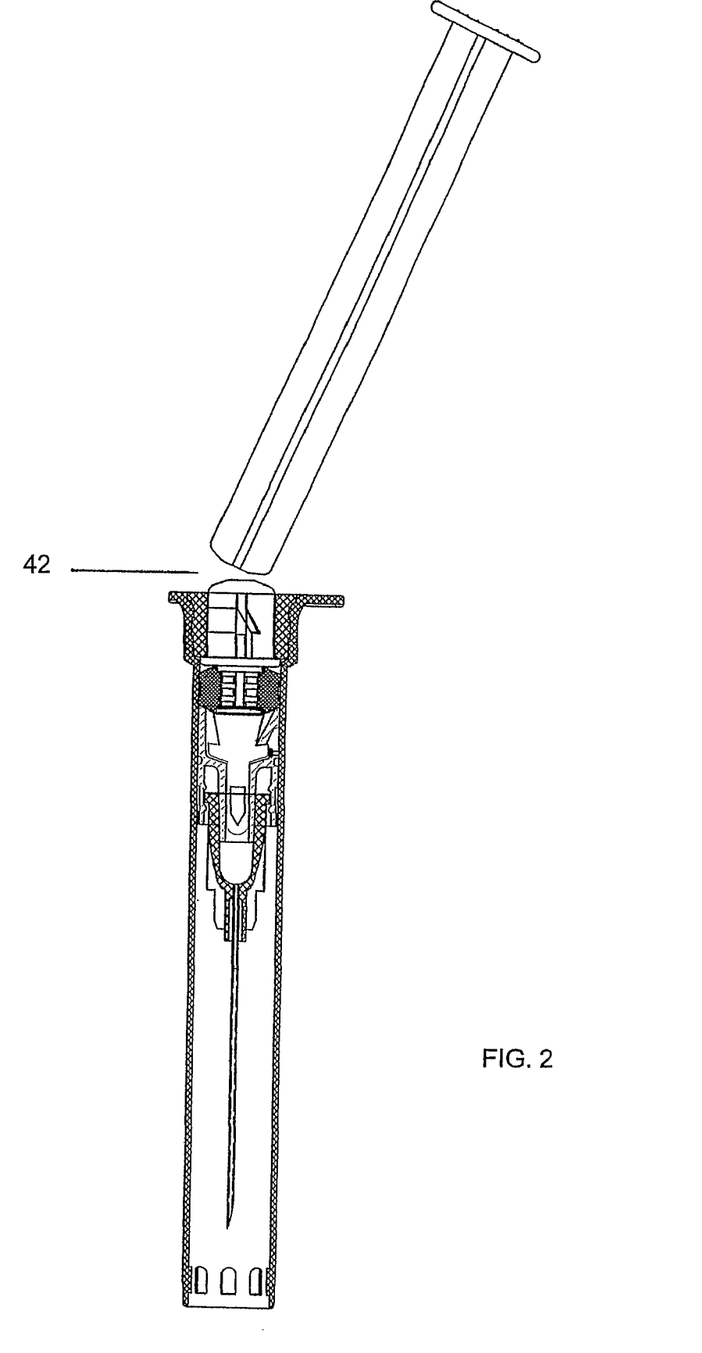
FIG. 2 is a partial sectional view of the syringe of FIG. 1 at the end of a retraction stroke.

When the fingers 90 pass the shoulders 82, they spring outwardly into a captive position as shown in FIG. 2. In the captive position, the head 34 cannot be again inserted towards the leading end 26 of the syringe 20, as the fingers 90 are in captive engagement with the shoulders 82.

In addition, the plunger 28 cannot be further retracted from the barrel 22 if an attempt is made to longitudinally displace the stem 29 in the retraction direction, as the shoulder of the head 38 engages the abutment surface 81 of the locking bush 70. Accordingly, the plunger 28 is isolated against significant movement in either an insertion or retraction direction along the longitudinal axis X.

At this point, the medical practitioner may apply a force to the stem 29 in a direction which is perpendicular to the longitudinal axis X. The force causes the stem 29 to rupture at the frangible region 42. The filly retracted syringe 20, with the ruptured stem 29, is shown in FIG. 2. The syringe 20 is then disposed of in a sharps container.

Figures 7, 10:
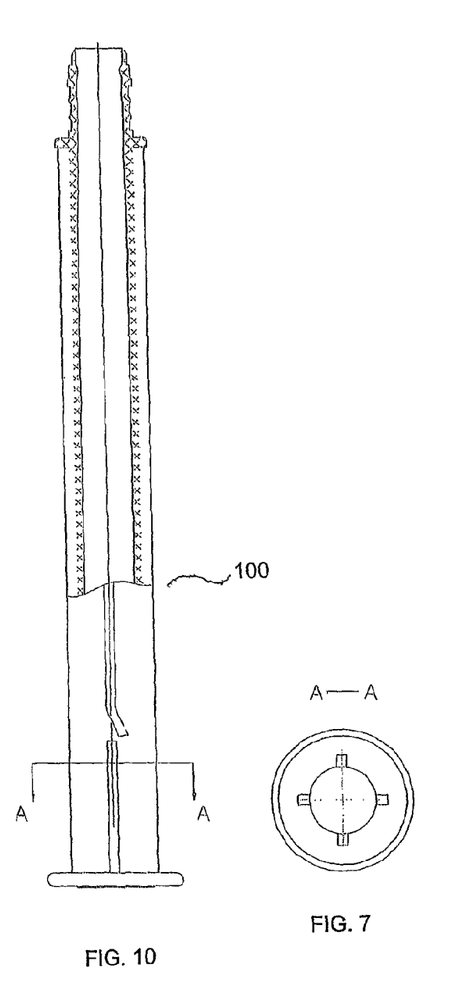
FIG. 7 is a top view of the locking bush in a closed position.
FIG. 10 is a partial cut-away view showing the barrel and plunger of a syringe according to a second embodiment.
Figure 8:
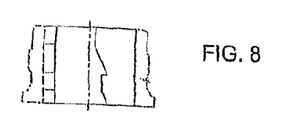
FIG. 8 is a side view depicting a locking bush in a closed position.
Figure 9:
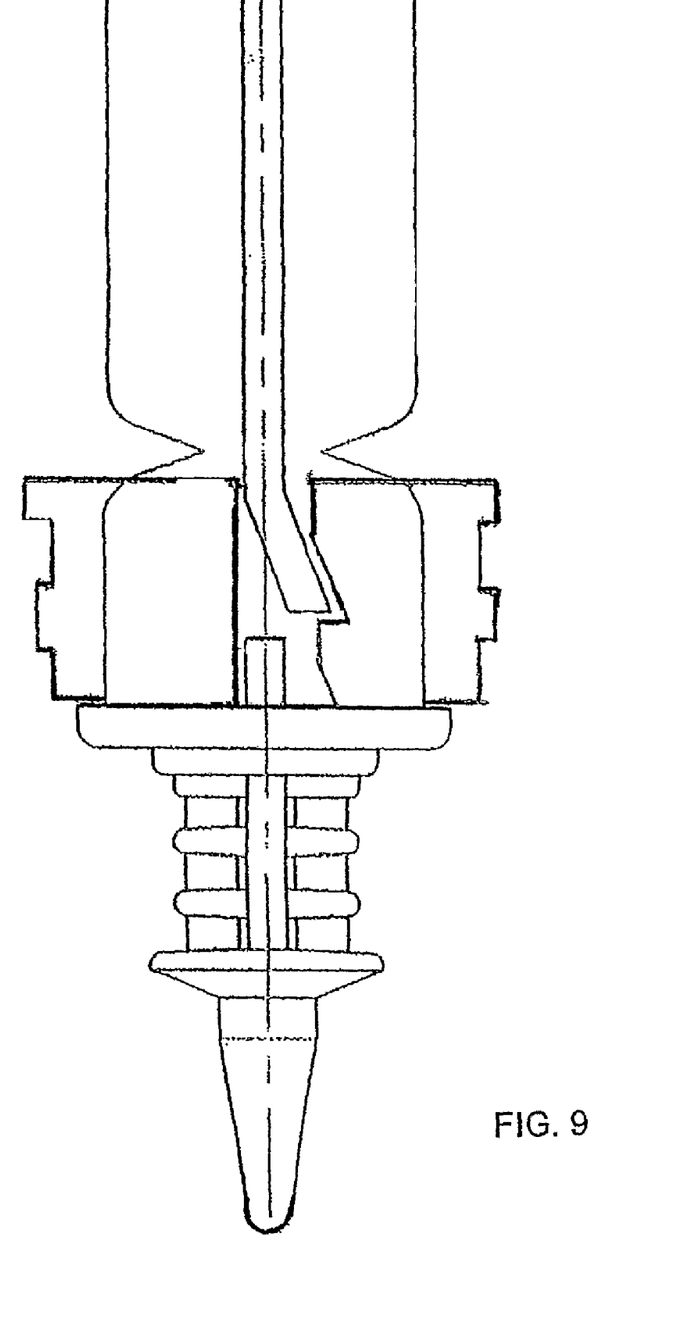
FIG. 9 is a partial view of the syringe plunger and locking bush.
Figure 11:
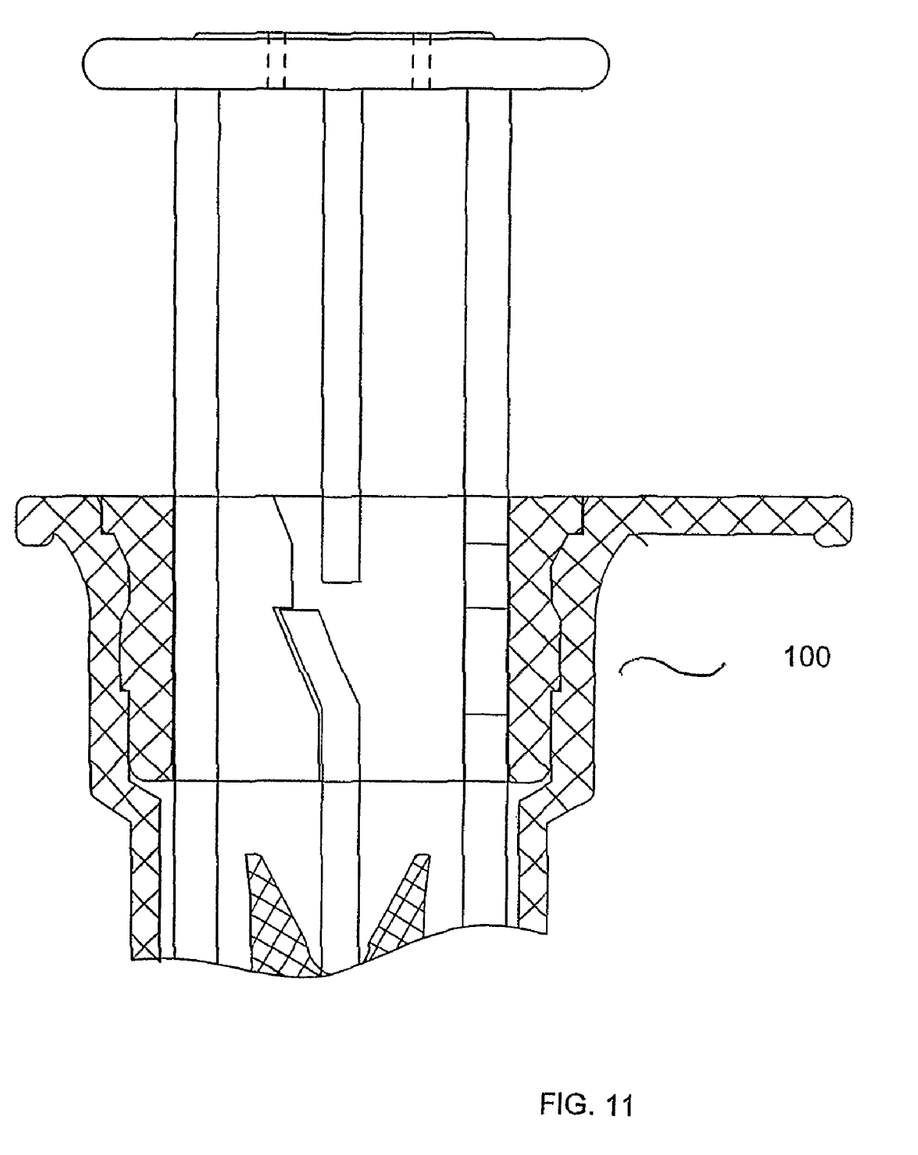
FIG. 11 is a partial cross-sectional view showing the plunger of FIG. 10 locked within the barrel.
Figure 12:
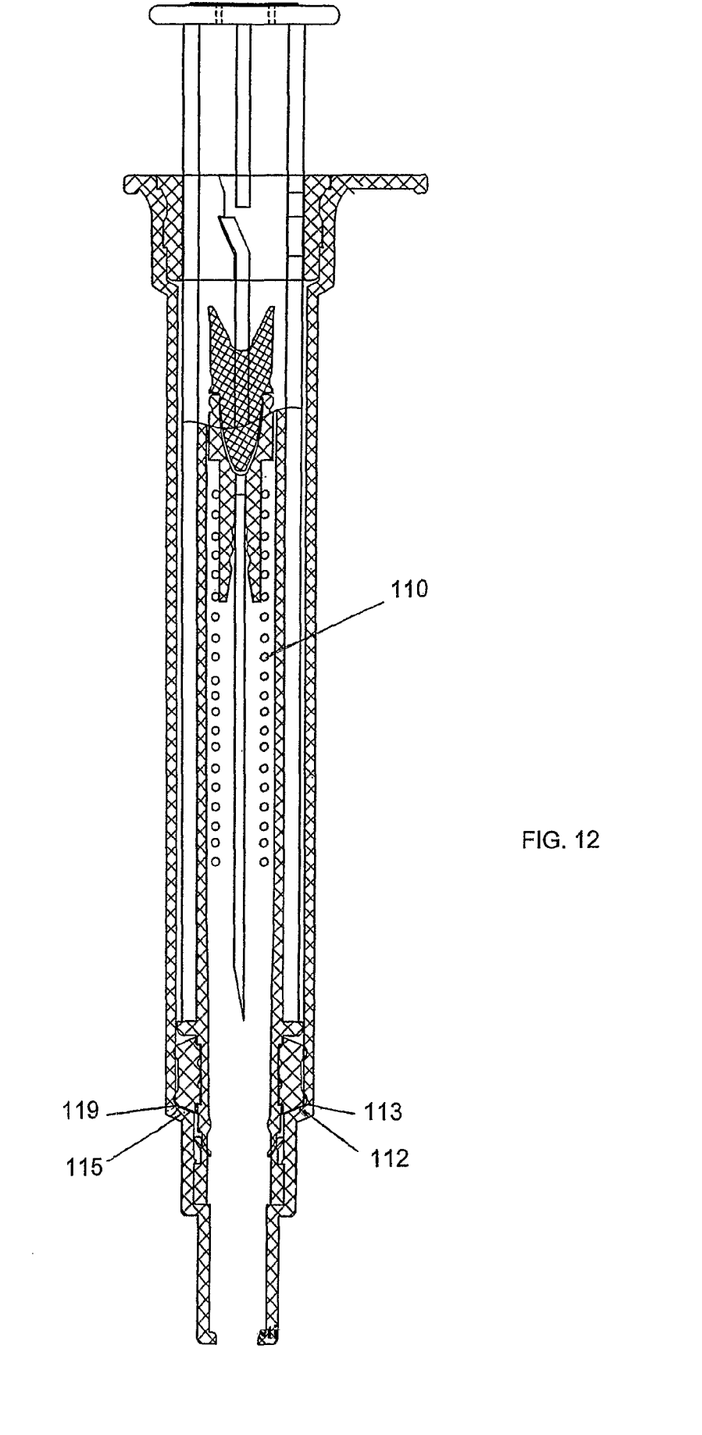
FIG. 12 is a cross-sectional view showing the syringe of the second embodiment after retraction of the needle tip.

A single use, non-retractable syringe 100 according to a second embodiment is shown in FIGS. 10 to 12. Like reference numerals are used to indicate like features.

In the second embodiment, the first engagement formation in the form of fingers 90 are directed generally towards the trailing end 30 of the syringe 20. In addition, the fingers 90 are located towards the rear of the stem 29, such that engagement between the first engagement formation defined by fingers 90 and the third engagement formation defined by shoulders 82 occurs toward the end of an insertion stroke.

In the second embodiment, during the administering of an injection, when the head 34 is at or near the end of the stroke, the fingers 90 engage with the shoulders 82 in a captive position, such that captive engagement occurs between the stem 29 and the locking bush 70. Accordingly, the syringe 100 is locked such that the plunger 28 cannot be withdrawn, and accordingly, the syringe 100 cannot be reused. In this state, the head 34 is longitudinally isolated and retraction of the head away from the leading end 26 to enable refilling of the barrel 22 with fluid is prevented.

In the second embodiment, the barrel 22 has a fourth engagement formation 113 defined by a restriction. As seen in FIG. 12, the cross-sectional area within the barrel 22 is locally reduced at the shoulder 115. In this embodiment, the head 34 has a shoulder 119 defining the second engagement formation. The shoulder 119 may be formed on the leading end of the piston seal 36, as shown in FIG. 12. When the shoulder 119 of the head 34 contacts the shoulder 115 of the barrel 22, the plunger 28 cannot be longitudinally displaced further in an insertion direction towards the leading end 26.

FIG. 12 shows a syringe of the second embodiment having an auto-retractable needle tip. After an injection has been administered and the stem 29 engages with the locking bush 70, the needle tip 24 and needle hub 50 are urged by a spring 110 into the barrel 22.

Advantageously, the fingers 90 are located at a suitable position on the stem 29 to permit a small amount of longitudinal movement of the plunger 28 after engagement of the locking bush 70 with the stem 29, and hence back-flushing of the barrel with blood if desired.

Advantageously, the syringe of the second embodiment cannot be refilled after the completion of an insertion stroke.

Although the invention has been described with reference to specific examples, it will be appreciated by those skilled in the art that the invention may be embodied in many other forms.

The invention claimed is:

1. A single use syringe having a leading end, a trailing end and a longitudinal axis,
    said syringe comprising:
    a longitudinally extending hollow barrel configured to contain a volume of liquid,
    a plunger having a stem, a head and a needle tip, said head being longitudinally displaceable within said barrel, said stem having a first engagement formation and said head having a shoulder defining a second engagement formation, wherein said first engagement formation includes a resilient finger having a fixed base portion and a resilient tip, said finger being angularly offset relative to said longitudinal axis, and said resilient tip of said finger directed generally towards said leading end of said syringe and directed generally away from said trailing end of said syringe; and
    a locking bush longitudinally fixed within said barrel, said bush having an aperture adapted to receive said stem, permitting the stem to slide longitudinally relative to said bush, said bush having a third engagement formation, said bush, also having an abutment surface defining a fourth engagement formation;
    wherein said plunger is longitudinally displaceable in a retraction direction away from the leading end to a captive position in which said resilient tip of said first engagement formation captively engages said third engagement formation thereby preventing the stem from being longitudinally displaced in an insertion direction toward the leading end from said captive position, and wherein said fourth engagement formation is engageable with said second engagement formation if an attempt is made to longitudinally displace said stem in the retraction direction from said captive position.

2. The syringe of claim 1, wherein said third engagement formation includes a shoulder formed within said aperture of said locking bush.

3. The syringe of claim 2, wherein said stem includes a web extending parallel to said longitudinal axis, a base portion of said finger being integrally formed with said web.

4. The syringe of claim 3, wherein the aperture formed in said locking bush includes a slot adapted to receive said web.

5. The syringe of claim 2, wherein said stem includes a plurality of webs radially equi-spaced about said longitudinal axis.

6. The syringe of claim 5, wherein the aperture of said locking bush includes a plurality of radially equi-spaced slots adapted to receive said plurality of webs.

7. The syringe of claim 1, wherein a circumferential outer wall of said locking bush includes a fifth engagement formation which is engaged with a sixth engagement formation defined by an inner wall of said barrel to longitudinally fix the locking bush.

8. The syringe of claim 1, wherein said locking bush is formed from two generally semi-circular segments.

9. The syringe of claim 8, wherein said segments are integrally formed and connected to each other with a flexible web.

10. A single use syringe comprising:
    a leading end, a trailing end and a longitudinal axis;
    a longitudinally extending hollow barrel;
    a plunger having a stem, a head and a needle tip, said head being longitudinally displaceable within said barrel, said stem having a first engagement formation and said head having a shoulder defining a second engagement formation, wherein the plunger forms a liquid tight seal against the internal wall of the barrel, said first engagement formation includes a resilient finger having a fixed base portion and a resilient tip, said finger being angularly offset relative to said longitudinal axis, and said resilient tip of said finger directed generally towards said leading end of said syringe and directed generally away from said trailing end of said syringe; and
    a locking bush longitudinally fixed within said barrel, said bush having an aperture adapted to receive said stem, permitting the stem to slide longitudinally relative to said bush, said bush having a third engagement formation, said bush also having an abutment surface defining a fourth engagement formation,
    wherein said plunger is longitudinally displaceable in a retraction direction away from the leading end to a captive position in which said resilient tip of said first engagement formation captively engages said third engagement formation thereby preventing the stem from being longitudinally displaced in an insertion direction toward the leading end from said captive position, and wherein, with the plunger in the captive position, said fourth engagement formation engages said second engagement formation when said stem is displaced longitudinally in the retraction direction from said captive position.

11. The syringe of claim 10, wherein said stem includes a web extending parallel to said longitudinal axis and wherein said finger is defined by a break in said web.

12. A single use syringe having comprising:
    a leading end, a trailing end and a longitudinal axis;
    a longitudinally extending hollow barrel in fluid communication with a needle tip;

a plunger having a stem, a head and a needle tip, said head being longitudinally displaceable within said barrel, said stem having a first engagement formation and said head having a shoulder defining a second engagement formation, wherein said first engagement formation includes resilient finger having a fixed base portion and a resilient tip, said finger being angularly offset relative to said longitudinal axis, and said resilient tip of said finger directed generally towards said leading end of said syringe and directed generally away from said trailing end of said syringe; and a locking bush longitudinally fixed within said barrel, said bush having an aperture adapted to receive said stem, permitting the stem to slide longitudinally relative to said bush, said bush having a third engagement formation, said bush also having an abutment surface defining a fourth engagement formation;

wherein said plunger is longitudinally displaceable in a retraction direction away from the leading end to a captive position in which said resilient tip of said first engagement formation captively engages said third engagement formation thereby preventing the stem from being longitudinally displaced in an insertion direction toward the leading end from said captive position, wherein, with the plunger in the captive position, said fourth engagement formation is engageable with said second engagement formation when the said stem is displaced longitudinally in the retraction direction from said captive position.

* * * * *